(12) United States Patent
Mooney et al.

(10) Patent No.: US 6,438,405 B1
(45) Date of Patent: Aug. 20, 2002

(54) IMAGING SAFETY DEVICE

(75) Inventors: Matthew Mooney, Westford; Bernard J Savord, Andover, both of MA (US); Patrick G Rafter, Windham, NH (US)

(73) Assignee: Koninklijke Philips Electronics, N.V., Eindhoven (NL)

(*) Notice: Subject to any disclaimer, the term of this patent is extended or adjusted under 35 U.S.C. 154(b) by 0 days.

(21) Appl. No.: 09/560,490

(22) Filed: Apr. 28, 2000

(51) Int. Cl.[7] .................................. A61B 5/05
(52) U.S. Cl. ............... 600/427; 600/407; 600/411; 600/439
(58) Field of Search ............... 600/427, 411, 600/437, 439, 449; 604/503, 504, 505

(56) References Cited

U.S. PATENT DOCUMENTS

| | | | | |
|---|---|---|---|---|
| 5,437,278 A | * | 8/1995 | Wilk | |
| 5,464,014 A | * | 11/1995 | Sugahara | |
| 5,696,492 A | * | 12/1997 | Sakamaki et al. | |
| 5,733,259 A | * | 3/1998 | Valcke et al. | |
| 5,827,196 A | | 10/1998 | Yeo et al. | 600/509 |
| 5,871,446 A | * | 2/1999 | Wilk | |
| 5,876,349 A | | 3/1999 | Wang et al. | 600/518 |
| 5,967,994 A | | 10/1999 | Wang | 600/509 |
| 6,246,897 B1 | * | 6/2001 | Foo et al. | |

* cited by examiner

Primary Examiner—Marvin M. Lateef
Assistant Examiner—Runa Shah Qaderi
(74) Attorney, Agent, or Firm—John Vodopia

(57) ABSTRACT

An imaging system in which a patient monitoring device, that monitors physiological parameters of a patient and outputs a signal indicating values for the parameters, is in communication with a patient imaging system. The patient imaging system includes an imaging probe that directs energy into and receives energy from a patient; and a signal analyzer, in communication with the patient monitoring device, that analyzes the signal from the patient monitoring device and outputs a signal indicating irregularities in parameters monitored. A control unit monitors the signal from the signal analyzer and, when a predetermined signal is output, issues an alarm to the operator of the patient imaging system. The control unit can also be programed to reduce the output power of the imaging probe and/or alert a central monitoring facility in response to the output of the signal analyzer.

19 Claims, 5 Drawing Sheets

| Device | Output | Action |
|--------|--------|--------|
| ECG | PVC | Alarm |
| ECG | Multiple PVC | Alarm, Reduce Output |
| ECG | Major Arrhythmia | Alarm, Reduce Output, Alert |
| BPM | ΔBP near Limits | Alarm |
| BPM | ΔBP outside Limits | Alarm, Reduce Output |
| O2 | O2 near Limits | Alarm |
| O2 | O2 outside Limits | Alarm, Reduce Output |

FIG. 3

IMAGING SAFETY DEVICE

BACKGROUND OF THE INVENTION

The present invention relates to methods and apparatus which, connect and integrate an imaging system with patient monitoring devices to inform the user of the imaging system about detected irregularities. The present invention is particularly useful in integrating an ultrasound imaging system and an ECG monitor with known heart function abnormality detectors.

Ultrasound imaging is usually performed at the highest power level setting provided by an ultrasound system. Recent advances in ultrasound imaging include the use of contrast agents to enhance ultrasound returns. Contrast agents are substances which strongly interact with ultrasound waves and return echoes which may be clearly distinguished from those returned by blood and tissue. With the use of contrast agents, lower power levels can be utilized for normal scanning procedures. However, the use of contrast agent lead to imaging methods involving repeated high power scans to disrupt contrast agent. This is useful for two reasons: first, the high power scans bust (or disrupt) contrast agent creating an easily detectable disturbance; and second, once the contrast agent has been disrupted, subsequent viewing will show the re-population of contrast agent, allowing an extrapolation of flow rates, including perfusion.

Presently, new higher power modes of imaging with and without contrast agent are being explored. Indications are that future methods may require ever increasing power level to obtain some measurement or image. Such high power scanning is causing increasing unease in the medical industry, which is questioning possible side-effects produced by such ultrasound procedures.

Such safety concerns have lead to advances in ultrasound technology, for example the use of modified waveforms to gently increase the applied acoustic energy. However, the present inventors have recognized a need for additional monitoring of a patient's condition, and that such additional monitoring must be integrated with an ultrasound system. The main reason for such integration is that many sonographers are not trained to operate or interpret the output of other patient monitoring devices. The present inventors have also realized that such integration should be expanded to allow automated control of the ultrasound system in the event of an emergency.

SUMMARY OF THE INVENTION

The present invention integrates an abnormality detection function with an imaging system. A method is described in which an imaging system receives signals from a patient monitoring device, during an imaging procedure, and performs abnormality detection thereon. When an abnormality is discovered, an action database is consulted and appropriate actions, i.e. issuance of an alert or an alarm, and modification of the operation of the imaging system, are implemented.

The present invention also provides a medical device, including an imaging system, in which a patient monitoring device monitors physiological parameters of a patient and outputs a signal, indicating values for the parameters, to an imaging system. The imaging system includes an imaging probe that directs energy into and receives energy from a patient, and a signal analyzer, in communication with the patient monitoring device, that analyzes the signal from the patient monitoring device and outputs a signal indicating irregularities in parameters monitored. A control unit, in the imaging system, monitors the signal from the signal analyzer and, when a predetermined signal is output, issues an alarm to the operator of the patient imaging system. The control unit can also be programed to issue an alarm, reduce the output power of the imaging probe and/or alert a central monitoring facility in response to the output of the signal analyzer.

BRIEF DESCRIPTION OF THE DRAWINGS

These and other objects and advantages of the invention will become apparent and more readily appreciated from the following description of the preferred embodiments, taken in conjunction with the accompanying drawings of which:

FIG. 3 is an example of a database used by monitoring routines in accordance with the preferred embodiment of the present invention.

DESCRIPTION OF THE PREFERRED EMBODIMENTS

Figure 1:
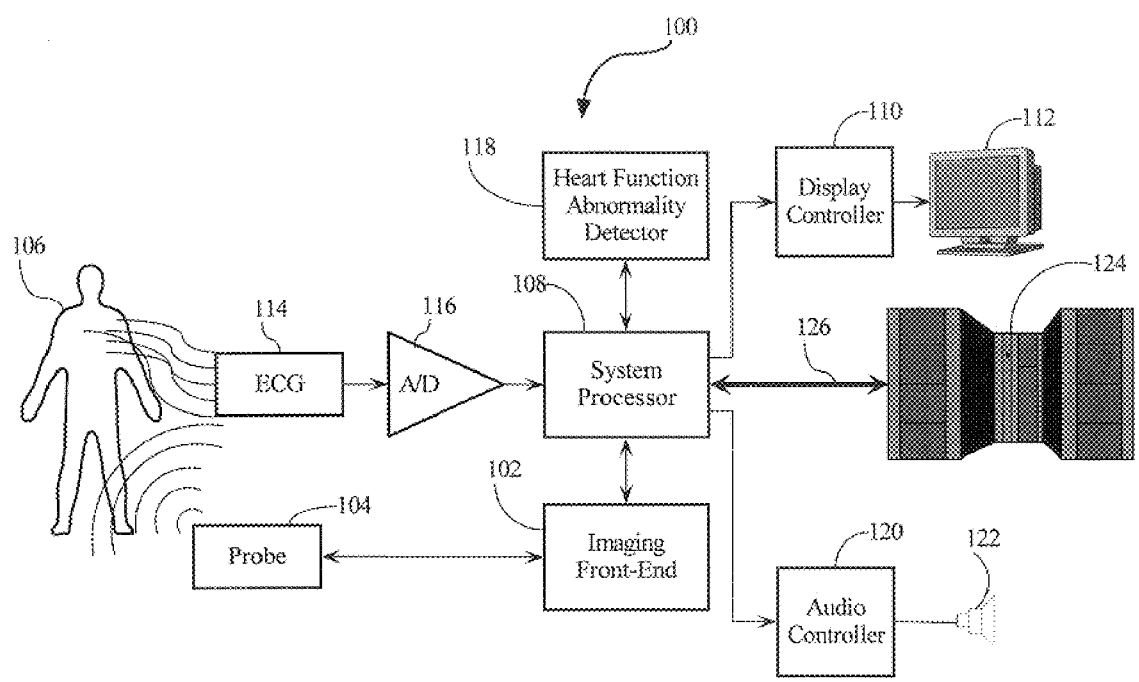
FIG. 1 is a block diagram of an imaging system in accordance with a preferred embodiment of the present invention.

Reference will now be made in detail to the preferred embodiments of the present invention, examples of which are illustrated in the accompanying drawings, wherein like reference numerals refer to like elements throughout.

The present invention provides an imaging system that receives input from a patient monitoring unit, analyzes the input, and issues an alarm to an operator of an ultrasound system when an abnormality occurs. In conjunction with the alarm, parameters that affect the output of imaging energy can also be adjust to, for example, change the output power, transmit duration, line rate, or transmit frequency. Signals that affect other systems may also be adjusted, such as outputting a signal that causes an IV delivery system to change an IV infusion rate. In the case of a networked imaging system, an alert can be issued, notifying a remote terminal of the situation.

The detailed description which follows is presented in terms of routines and symbolic representations of operations of data bits within a memory, associated processors, and possibly networks, and network devices. These descriptions and representations are the means used by those skilled in the art effectively convey the substance of their work to others skilled in the art. A routine is here, and generally, conceived to be a self-consistent sequence of steps or actions leading to a desired result. Thus, the term "routine" is generally used to refer to a series of operations performed by a processor, be it a central processing unit of an ultrasound system, or a secondary processing unit of such an ultrasound system, and as such, encompasses such terms of art as "program," "objects," "functions," "subroutines," and "procedures."

In general, the sequence of steps in routines require physical manipulation of physical quantities. Usually, though not necessarily, these quantities take the form of electrical or magnetic signals capable of being stored, transferred, combined, compared or otherwise manipulated. Those of ordinary skill in the art conveniently refer to these signals as "bits", "values", "elements", "symbols", "characters", "images", "terms", "numbers", or the like. It should be recognized that these and similar terms are to be associated with the appropriate physical quantities and are merely convenient labels applied to these quantities.

In the present case, the routines and operations are machine operations to be performed in conjunction with human operators. Useful machines for performing the operations of the present invention include the AGILENT TECHNOLOGIES, INC.'s SONOS 5500 and other similar devices. In general, the present invention relates to method steps, software, and associated hardware including computer readable medium, configured to store and/or process electrical or other physical signals to generate other desired physical signals.

The apparatus set forth in the present application may be specifically constructed for the required purpose, e.g. ultrasound imaging, but the methods recited herein may operate on a general purpose computer or other network device selectively activated or reconfigured by a routine stored in the computer and interface with the necessary ultrasound imaging equipment. The procedures presented herein are not inherently related to any particular ultrasonic system, computer or other apparatus. In particular, various machines may be used with routines in accordance with the teachings herein, or it may prove more convenient to construct more specialized apparatus to perform the required method steps. In certain circumstances, when it is desirable that a piece of hardware possess certain characteristics, these characteristics are described more fully in the following text. The required structures for a variety of these machines may appear in the description given below. Machines which may perform the functions of the present invention include those manufactured by such companies as AGILENT TECHNOLOGIES, INC., ATL ULTRASOUND, INC., as well as other manufacturers of imaging equipment.

With respect to the software described herein, those of ordinary skill in the art will recognize that there exists a variety of platforms and languages for creating software for performing the procedures outlined herein. Those of ordinary skill in the art also recognize that the choice of the exact platform and language is often dictated by the specifics of the actual system constructed, such that what may work for one type of system may not be efficient on another system.

FIG. 1 is a block diagram of an imaging system 100 in accordance with a preferred embodiment of the present invention. It will be appreciated by those of ordinary skill in the relevant arts that the imaging system 100, as illustrated in FIG. 1, and the operation thereof as described hereinafter is intended to be generally representative such systems and that any particular system may differ significantly from that shown in FIG. 1, particularly in the details of construction and operation of such system. As such, the imaging system 100 is to be regarded as illustrative and exemplary and not limiting as regards the invention described herein or the claims attached hereto.

The imaging System 100 generally comprises an imaging front end 102 which controls a probe/transmitter 104 to transmit to, and possibly receive energy from, a patient 106. The imaging front-end 102 operates under control of a system processor 108. When receiving data, the system processor 108 forms data for creating an image on a monitor 112 using a display controller 110. The imaging system 100 also includes a patient monitoring device, in this case an ECG monitoring unit 114, that outputs monitoring data. Those of ordinary skill in the art will recognize a variety of patient monitoring devices exist which are suitable for the detection of physical quantities associated with the well being of the patient, e.g. blood pressure monitors, oxygen level monitors, etc.

The ECG monitoring unit 114 may be anyone of a plurality of known devices available from a number of suppliers, including AGILENT TECHNOLOGIES, INC. The output format of the ECG monitoring device 114 is defined by the suppler, but as shown in FIG. 1, typically needs to be A/D converted by an A/D converter 116. The output of the A/D converter 116 is received by the system processor 108 and forwarded to a heart function abnormality detector 118. The heart function abnormality detector 118 performs known arrhythmia detection processing and outputs a signal when an arrhythmia is detected. Known ECG based heart function abnormality detectors include those disclosed in U.S. Pat. Nos. 5,967,994, 5876,349, and 5,827, 196, each of which is incorporated herein by reference.

In addition to forwarding the data to the heart function abnormality detector 118, the system processor 108, as is known in the art, also causes the display controller 110 to overlay an ECG trace on the image being displayed on the monitor 112. Such an overlay can be placed at a variety of locations on the imaged displayed by the monitor 112

When the heart function abnormality detector 118 outputs a signal indicating a heart function abnormality, the system processor 108 can implement a variety of actions. At a most basic level, an alarm can be output to speaker 122, via audio controller 120. Additionally, the audio alarm can be supplemented with a visual alarm on the monitor 112. For more serious abnormalities, parameters controlling the waveform output by the transducer 104 can be adjusted so as to, for example, attenuate the power of the waveform. Known heart function abnormality detectors output a variety of signals indicating various aspects of the ECG signal. The response of the system processor 108 can be modified to produce differing results depending on the signal output by the heart function abnormality detector 118. For example, in the case of a severe arrhythmia, the system processor 108 can instruct the imaging front end 102 to stop emitting energy. Additionally, an alert can be dispatched to a doctor or an emergency response team. This may be done by sending a message to a centralized patient monitoring facility 124 via communications interface 126 (such as a LAN or other connection).

As used herein the term "alarm" refers to a message, either audio or visual, given locally to the operator of the imaging system. The term "alert" refers to a message given remotely, though what ever means are available, to advise personal not located at the exam location.

FIG. 1 shows an example of an imaging system 100 wherein the heart function abnormality detector 118 is considered a separate logical block. Those of ordinary skill in the art will recognize that the heart function abnormality detector 118 can be formed using software, hardware or a combination thereof. Specific examples of ultrasound imaging systems having heart function abnormality detectors formed in hardware and software are discussed herein after. However, it is stressed that either solution is acceptable with the choice of configuration being left up to the system designer.

Figure 2:
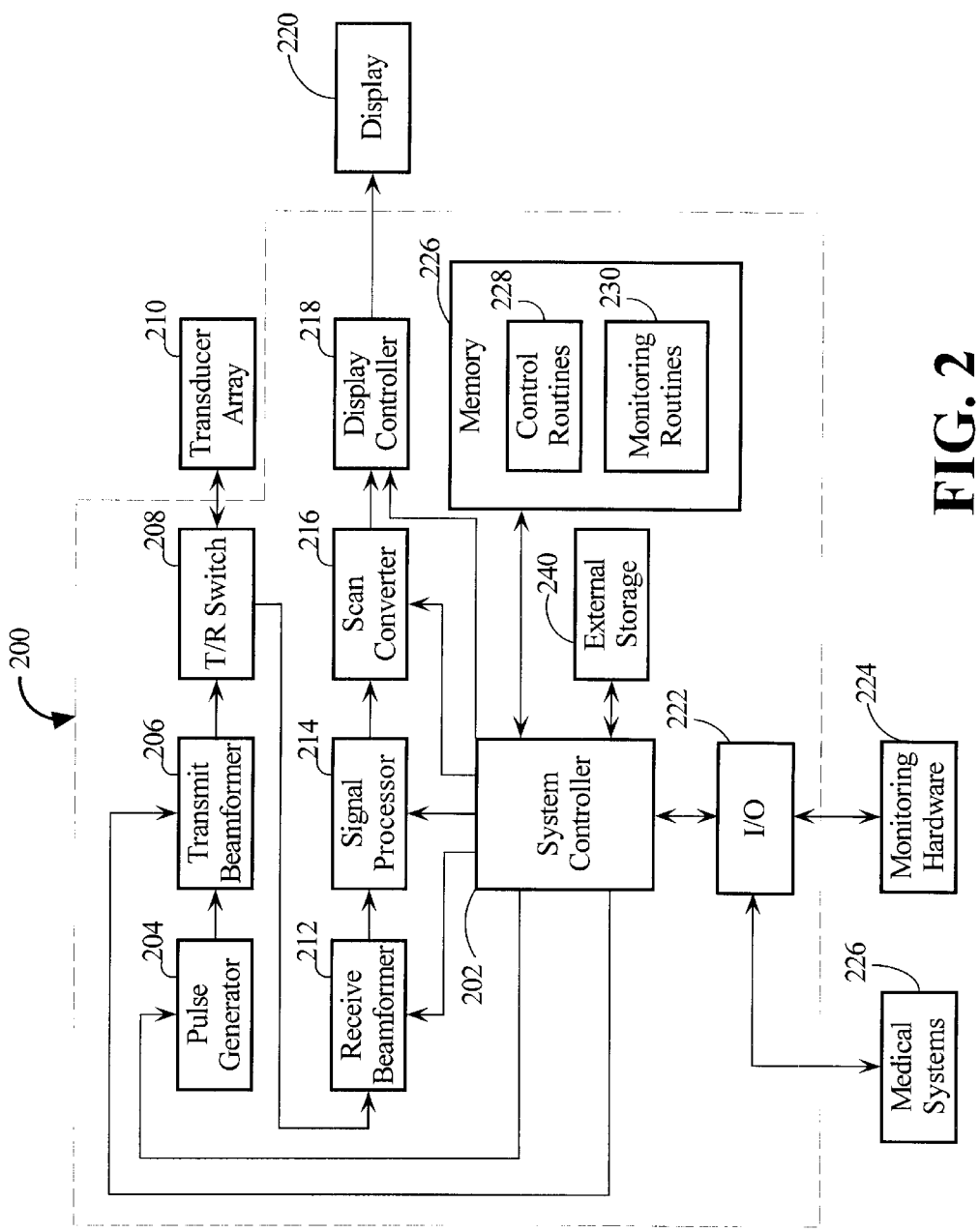
FIG. 2 is a block diagram of an ultrasound system in accordance with the preferred embodiment of the present invention.

FIG. 2 is a block diagram of an ultrasound system 200 in accordance with the preferred embodiment of the present invention. The ultrasound imaging system 200 is a more specialized case of the imaging system 100 (FIG. 1), in that the imaging system 200 is an ultrasound system. The ultrasound system 200, as shown, is a traditional system with most functional blocks corresponding to a discrete hardware structures. More to the point, FIG. 2 illustrates and example of a configuration in which a central processor performs heart function abnormality detection based on a program stored in a memory (although dedicated hardware solutions are possible).

A transmit beamformer 206 is coupled through a transmit/receive (T/R) switch 208 to a transducer array 210, which includes an array of transducer elements. The T/R switch 208 typically has one switch element for each transducer element. The transmit beamformer 206 receives transmit pulse sequences from a pulse generator 204. The transducer array 210, energized by the transmit beamformer, transmits ultrasound energy into a region of interest in a patient's body and receives reflected ultrasound energy, or echoes, from various structures and organs within the patient's body. As is known in the art, by appropriately delaying the pulses applied to each transducer element by transmit beamformer 206, a focused ultrasound beam is transmitted.

The transducer array 210 is coupled through the T/R switch 208 to a receive beamformer 212. Ultrasound energy from a given point within the patient's body is received by the transducer elements at different times. The transducer elements convert the received ultrasound energy to transducer signals which may be amplified, individually delayed and then summed by the receive beamformer 212 to provide a beamformer signal that represents the received ultrasound level along a desired receive line. The receive beamformer 212 may be a digital beamformer including an analog-to-digital converter for converting the transducer signals to digital values. As known in the art, the delays applied to the transducer signals may be varied during reception of ultrasound energy to effect dynamic focusing. The process is repeated for multiple scan lines to provide signals for generating an image of the region of interest in the patient's body. The receive beamformer 212 may, for example, be a digital beamformer of the type used in the AGILENT SONOS 5500 ultrasound system manufactured and sold by AGILENT TECHNOLOGIES, INC.

The scan pattern may be a sector scan, wherein scan lines typically originate at the center of the transducer array 210 and are directed at different angles. Linear, curvilinear and other scan patterns may also be utilized. Furthermore, the scan pattern may be two-dimensional or three-dimensional. In an alternative system configuration, different transducer elements are used for transmit and receive. In that configuration, the T/R switch 208 is not required, and the transmit beamformer 206 and the receive beamformer 212 are connected directly to the respective transmit and receive transducer elements.

The beamformer signals are applied to a signal processor 214 which processes the beamformer signal for improved image quality. The output of the signal processor 214 is supplied to a scan converter 216 which converts sector scan or other scan pattern signals to conventional raster scan display signals. The output of the scan converter 216 is supplied to a display controller 218 which causes the display unit 220 to display an image of the region of interest in the patient's body as represented by the output of the scan converter. In the case of a three-dimensional scan pattern, the scan converter 216 may be replaced by an image data buffer that stores the three-dimensional data set and a processor that converts the three-dimensional data set to a desired two-dimensional image.

A system controller 202 provides overall control of the system. The system controller 202 performs timing and control functions and typically includes a microprocessor operating under the control of control routines 228, including monitoring routines 230, which are stored in a memory 226. The system controller 202 also utilizes the memory 226 to store intermediate values, including system variables describing the operation of the ultrasound imaging system 200. For example, the monitoring routines 230 store and retrieve various parameters necessary for operation from the memory 226. External storage 240 may be utilized for more permanent and/or transportable storage of data. Examples of suitable external storage devices include a floppy disk drive, a CD-ROM drive, a videotape unit, etc . . .

The system controller 202 is also connected to an I/O unit 222, for example an RS 232 interface, for connection to monitoring hardware 224, such as an ECG monitor, a blood pressure monitor, or an oxygen level sensor. The I/O unit 226 can also function as an interface to other medical systems, such as automated drug delivery systems that operate with (using contrast agents to provide localized drug delivery), or independent of, the ultrasound imaging system 200. The I/O unit 222 may also facilitate communication with an external computer system such as a centralized patient monitoring facility (FIG. 1) for issuing alerts.

When operating under the control of the monitoring routines 230, the system controller receives, through an I/0 interface 222, a data stream from the monitoring hardware 224. Using known algorithms, the system controller 202 monitors the data stream and when a heart function abnormality occurs, accesses routines in the monitoring routines to issue an alarm to the operator, send an alert to a remote location and/or modify the output of the transducer array 210. The way in which the system controller 202 reacts to an abnormality may be predefined using a number of techniques. One particularly advantageous way is for the memory 226 or external storage 240 to maintain a database relating the output of the monitoring hardware 224 to various actions. The monitoring hardware 224 can also undertake the task of signal analysis and output values to the imaging system 200 directing certain action, such as lowering the power level of the signal output by the transducer array 210. In this case the monitoring routines would simply monitor the monitoring hardware 224 for instructions.

FIG. 3 is one example of a table 300 relating the output of the monitoring hardware 224 to various actions. The table 300 provides for a plurality of records which relate a monitoring device, output from that device, and actions to take based on the output. Table 300 is shown in a simple form to facilitate explanation. Those of ordinary skill in the art will recognize that many enhancements and additions can be made to increase functionality and reduce storage space. In general, when the monitoring routines 230 (FIG. 2) issue a signal, such as an interrupt, based on an abnormal signal from the monitoring hardware 224, a search of the table 300 is made to locate entries for the device that caused the abnormal signal and matching outputs. Then, the system controller 202 causes the actions listed in the Action column to be executed. For example, if the monitoring routine responsible for monitoring ECG leads detects a major arrhythmia (which may be defined as a numerical range for a given signal), the system controller 202 directs an alarm (audio and/or visual) to issue from the ultrasound system 200, the power level of the transducer array to be reduced, and an alert to be issued to a centralized patient monitoring facility (FIG. 1).

The use of a table, similar to the table shown in FIG. 3, is advantageous in that a user interface can be constructed in which medical professionals can easily relate devices and outputs thereof to the actions. This allows programmers to concentrate on the technical (as opposed to medical) functions that implement the requested actions and handle receipt of the various outputs. As noted above, the table 300 is a highly simplified representation of a database for use in the present invention. Those of ordinary skill in the art will be able, from this description, to create appropriate data structures and routines for handling the data flow, errors, and security function required in a working environment.

Figure 4:
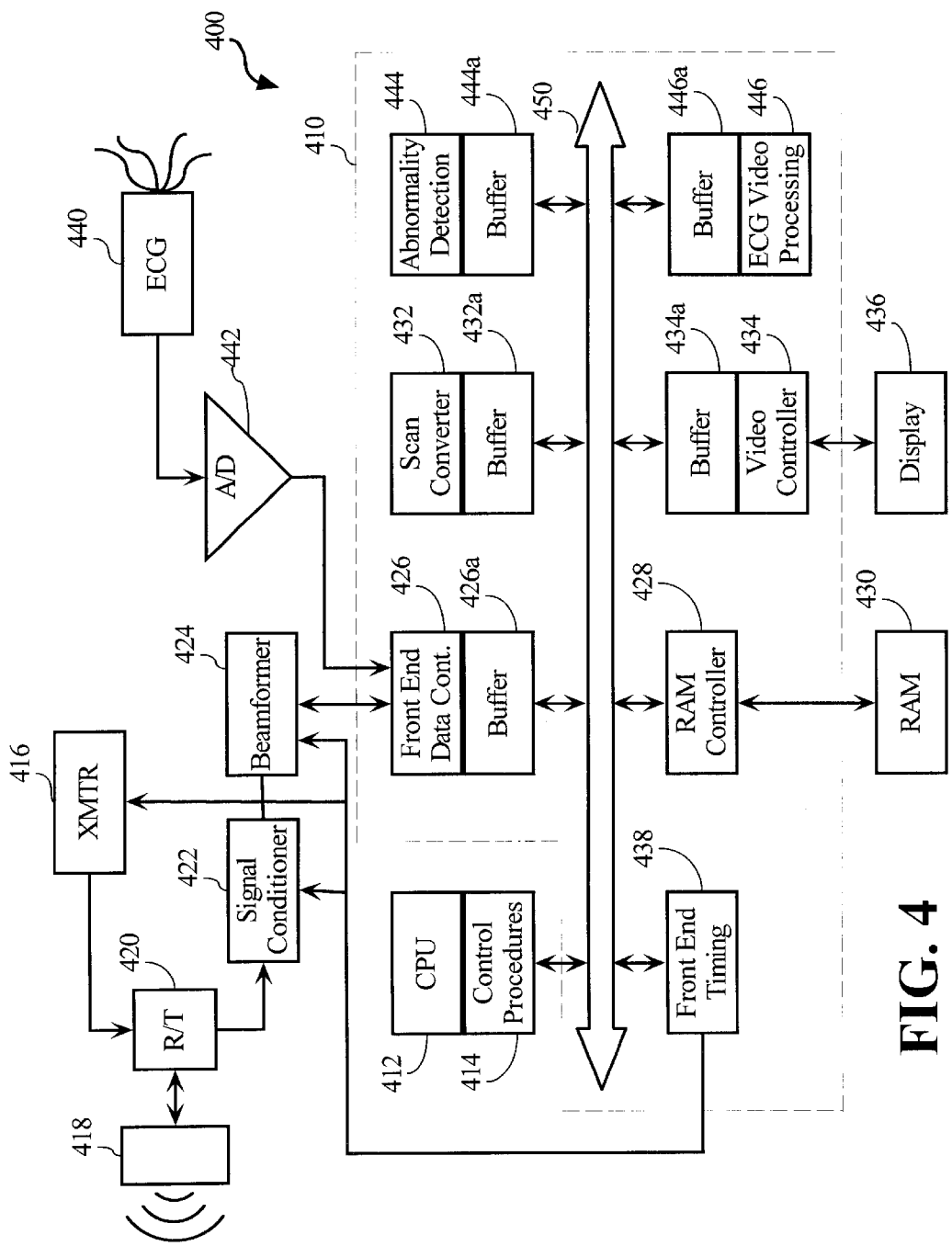
FIG. 4 is a block diagram of an ultrasound system in accordance with the preferred embodiment of the present invention.

FIG. 4 is a block diagram of an ultrasound system 400 in accordance with the preferred embodiment of the present invention. The ultrasound system 400 is configured around a central bus and a unified memory. In contrast to the ultrasound system 200, shown in FIG. 2, the ultrasound system 400 performs heart function abnormality detection on a dedicated circuit (although software driven solutions are possible).

The ultrasound system 400 includes a transducer 418 which, in the known manner, scans an ultrasound beam, based on a signal from a transmitter 416, through an angle. Backscattered signals are sensed by the transducer 418 and are fed through a received/transmit switch 420 to a signal conditioner 422 and, in turn, to a beamformer 424. The signal conditioner 422 receives the backscattered ultrasound analog signals and conditions those signals by amplification and forming circuitry prior to their being fed to the beamformer 424. Within the beamformer 424, the ultrasound signals are converted to digital values and are configured into "lines" of digital data values in accordance with amplitudes of the backscattered signals from points along an azimuth of the ultrasound beam.

The beamformer 424 feeds the digital values to an application specific integrated circuit (ASIC) 410 which incorporates the principal processing modules required to convert the digital values into video displayable data for feed to a display 436.

A front end data controller 426, receives the lines of digital data values from the beamformer 424 and buffers each line, as received, in an area of a buffer 426a. After accumulating a line of digital data values, the front end data controller 426 dispatches an interrupt signal, via a bus 450, to a shared central processing unit (CPU) 412. The CPU 412 executes control procedures 414 that are operative to enable individual, asynchronous operation of each of the processing modules within the ASIC 410. More particularly, upon receiving the interrupt signal, the CPU 412 causes the line of digital data values data residing in the buffer 426a to be fed to a random access memory (RAM) controller 428 for storage in a random access memory (RAM) 430.

As will hereafter be understood, RAM 430 may comprise one or plural memory modules, but all such memory modules are operated under control of the RAM controller 428 and, as such, thereby constitute a unified, shared memory. RAM 430 stores instructions and data for the CPU 412, lines of RF digital data values and data being transferred between individual modules in the ASIC 430, all under control of the RAM controller 428.

A front end timing controller 438 is controlled by one of the control procedures 414 to output timing signals to the transmitter 416, the signal conditioner 422 and the beam former 424 so as to synchronize their operations with the operations of the modules within ASIC 410. The front end timing controller 438 further issues timing signals which control the operation of the bus 450 and various other functions within the ASIC 410.

As aforesaid, the control procedures 414 operates the CPU 412 to enable the front end data controller 426 to move the lines of digital data values into the RAM controller 428 where they are then stored in RAM 430. Since the CPU 412 controls the transfer of lines of digital data values, it senses when an entire image frame has been stored in RAM 430. At this point, the CPU 412, in conjunction with the control procedures 414, recognizes that data is now available for operation by the scan converter 432, at which point, the CPU 412 notifies the scan converter 432 that it can access the frame of data from RAM 430 for processing.

To access the data in RAM 430 (via RAM controller 428), the scan converter 432 interrupts the CPU 412 to request a line of the data frame from RAM 430. Such data is then transferred to a buffer 432a of the scan converter 432, and is processed to put it into a displayable form. This process is repeated for each subsequent line of digital data values of the image frame from RAM 430. The resulting processed data is fed, via the RAM controller 428, into RAM 430 as video-ready data. The CPU 412 and the control procedures 414, via the interrupt procedure described above, sense the completion of the operation of the scan converter 432. The video controller 434, on a continuing basis, interrupts the CPU 412 which responds by causing a feed of lines of video data thereto from RAM 430 into a buffer 434a of the video controller 434 for display by the display monitor 436.

An ECG 440 (representative of a wide variety of patient monitoring devices that may be employed) output signals to an A/D converter 442, which passes the values to the front end data controller 426. The front end data controller 426, under control of the CPU 412, transfers the values output by the ECG 440 into RAM 430. An ECG video processing circuit reads the values (using the interrupt procedure described above), via a buffer 446a, and instructs the video controller 434 to overlay an ECG trace signal on top of the ultrasound display.

An abnormality detection circuit 444 also reads the values output by the ECG 440 from RAM 430 and performs known heart function abnormality detection thereon. When an abnormality is detected, the abnormality detection circuit 444 issues an interrupt to the CPU to start an abnormality process. If only an alarm is to be issued, the CPU 412 controls the transfer of data to an ECG video processing circuit 446 which, in turn, outputs a signal to the video controller 434 to cause a message to be displayed ion the display 436 (along with an audible signal). The message and mode of display can be adjusted based on the abnormality detected. In the event that a reduction in the output power of the transducer 418 is required, the abnormality detection circuit 444 issues an interrupt requesting such a reduction to the CPU 412. In turn, the CPU 412 instructs the front end timing controller 438 to issue a signal to the transmitter 416 lowering the output of the transmitter 418. If required, alerts can be passed, via bus 450, to other connected devices (not shown), such as a centralized patient monitoring facility (FIG. 1).

Figure 5:
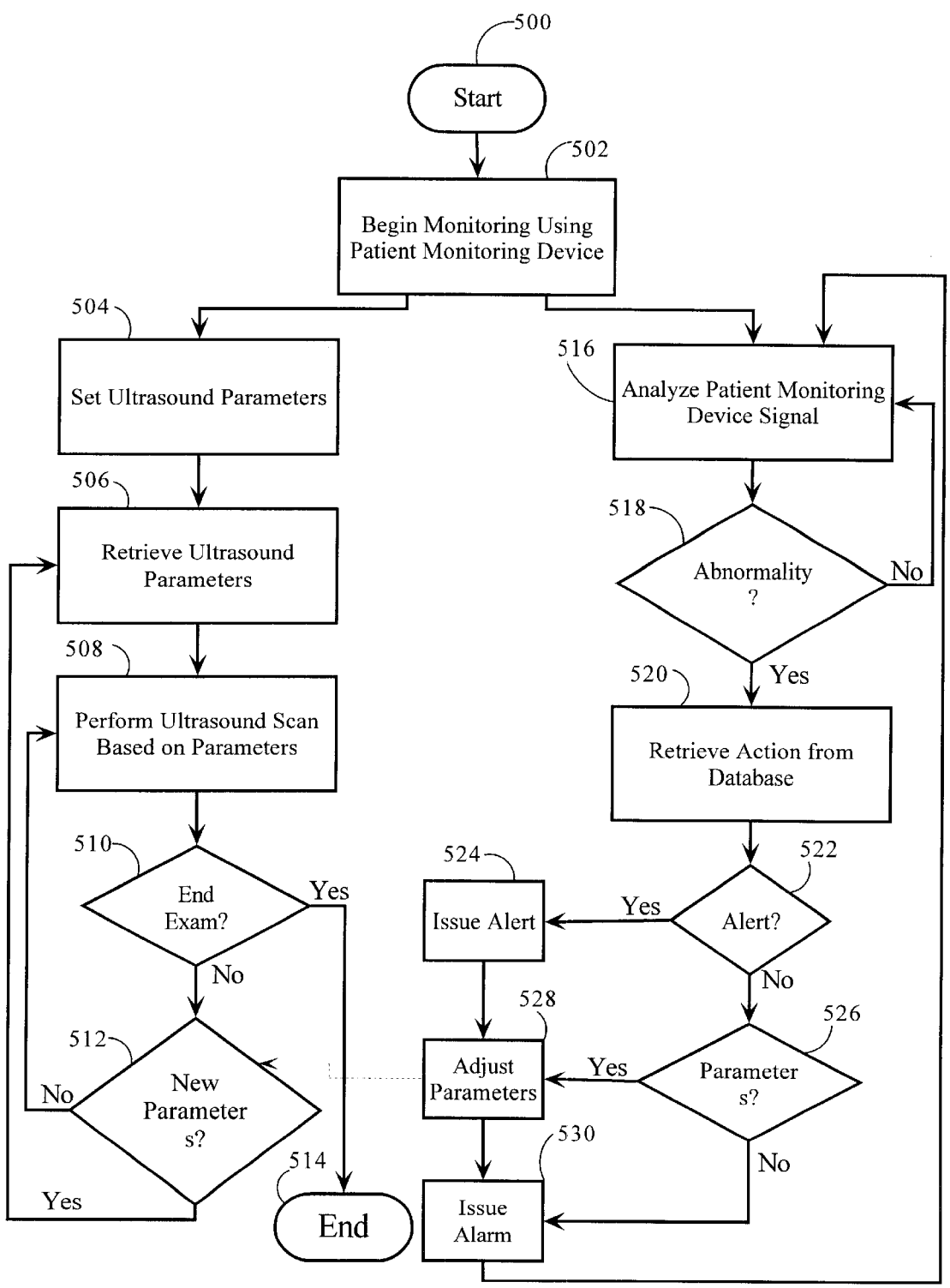
FIG. 5 is a flow chart of a method in accordance with a preferred embodiment of the present invention.

FIG. 5 is a flow chart of a method in accordance with a preferred embodiment of the present invention. The method may, where practical, be embodied in a routine to be executed by a general processing unit alone or in connection with a specific purpose processing unit. The routine described in FIG. 5 is tailored toward a medical ultrasound system (such as is shown in FIG. 2 and 4) and the database 300 shown in FIG. 3. Those of ordinary skill in the art will recognize the applicability of the routine to other imaging systems and other file types.

The method starts in step 500. In step 502, the operator of the imaging system (described hereinafter in terms of an ultrasound system) commences monitoring of a patient using a patient monitoring device, such as an ECG. Thereafter, in step 504, parameters controlling the output of an ultrasound transducer are set, for example in dedicated registers. The parameters may be either automatically set based on operator selected imaging mode or manually set by the operator. Next in Step 506, ultrasound parameters are retrieved. Then in step 508, an ultrasound scan is performed using the retrieved parameters.

Periodically, for example after each line or each frame output/received, a check is made, in step 510, as to whether the exam has ended and if not an additional check is made, in step 512, as to whether the parameters have been changed. If the exam has ended, the routine ends in step 514 and the imaging system is taken out of scan mode and the patient monitoring device may be removed and powered down.

In step 512, if no new parameters have been stored in the registers, the routine returns to step 508 and the ultrasound scan is continued. If new parameters have been stored in the registers, the routine returns to step 506 and the new parameters are retrieved. Subsequently, in step 508, the ultrasound scan is continued based on the newly retrieved parameters. New parameters can be created an stored by a variety of sources. The operator could have adjusted them, an automated imaging mode may be automatically change the parameters to produce varying images, and/or the parameters may be adjusted by the present method based on the output of the patient monitoring device.

In parallel with steps 504 through 512, the routine processes the loop of steps 516 through 530. In step 516, the patient monitoring device signal is analyzed. As stated above, this can be performed through hardware, software, and/or a combination thereof. Thereafter, in step 518, a check is made as to whether an abnormality has occurred. If no abnormality is discovered, the analysis of step 516 is continued. If and when an abnormality is discovered in step 518, the actions corresponding to the abnormality are retrieved, for example from database 300 (FIG. 3), in step 520.

The action is analyzed in steps 522 and 526 and the appropriate actions are carried out in steps 524, 528 and 530. As shown in FIG. 5, actions are ranked in a hierarchal manner, with each level of action requiring the lower level action to also be performed. Those of ordinary skill in the art will recognize that this is but one possible configuration. If in step 522, the retrieved action is an alert, the imaging system issues an alert in step 524. As used herein an alert is triggered by a significant event which may require the expertise of someone other than a sonographer. It is anticipated that imaging systems are, and will become more so, connected to other hospital information systems. Thus, an alert triggers a message to be sent to a remote terminal, perhaps of a centralized patient monitoring facility, requesting the presence of, for example, a doctor. In this case, not only will the alert be issued, but, in step 528 the ultrasound parameters are adjusted, for example lowering the output power of the transducer to zero, and in step 530 an alarm is issued by the imaging system to the operator of the imaging system.

If the action does not include an alert, a check is made in step 526 as to whether the ultrasound parameters need adjusting. This may result in the lowering of the power output by the transducer in step 528, but maybe not to zero. Subsequently an alarm is issued to the operator in step 530.

If the action does not include either an alert or an adjustment to the ultrasound parameters, an alarm is issued, in step 530, to the user of the ultrasound system.

In any event, the routine continues to analyze the signal output by the patient monitoring device through a return to step 516. The routine will continue to loop through steps 516 through 530 until the patient monitoring device is disconnected.

In accordance with the foregoing, the present inventors have described an imaging system that receives additional data from a patient monitoring device, analyzes the additional data, and when an abnormality is detected implements a pre-determined action. This represents a significant advance over the prior art which merely displayed the output of an ECG on a monitor of an imaging system.

Although a few preferred embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A medical system comprising:
   a patient monitoring device That monitors physiological parameters of a patient and outputs a signal indicating values for the parameters; and
   an imaging system including:
      an imaging probe that directs energy into a patient;
      a signal analyzer, in communication with the patient monitoring device, that analyzes The signal from The patient monitoring device and outputs an abnormality signal indicating irregularities in parameters monitored; and
      a controller monitoring the signal from the signal analyzer and, when a predetermined abnormality signal is output, issues an alarm to an operator of the imaging system;
         wherein the controller, upon output of a predetermined signal by the signal analyzer changes The energy output by the imaging probe to a non-zero value.

2. A medical system, as set forth in claim 1, wherein the controller causes a visual representation of the data received from the imaging probe to be displayed on a monitor and wherein the controller is in communication with the patient monitoring device, the controller causing a visual representation of the data received from the patient monitoring device to be displayed on the monitor overlaying the visual representation of the data received from the imaging probe.

3. A medical system, as set forth in claim 1, wherein the patient monitoring device is an ECG monitor.

4. A medical system, as set forth in claim 1, wherein the patient monitoring device is an oxygen level monitor.

5. A medical system, as set forth in claim 1, wherein the patient monitoring device is a blood pressure monitor.

6. A medical system, as set forth in claim 1, wherein the imaging system further includes a communication interface for communicating with a remote device and wherein the controller, when a predetermined abnormality signal is output, sends a message to the remote device.

7. A medical system, as set forth in claim 1, wherein the imaging system further includes a database that references abnormality signals to actions to be taken and wherein the controller, upon receipt of an abnormality signal from the signal analyzer refers to the table and implements the actions to be taken referenced by the abnormality signal.

8. A method of imaging comprising:
   performing a scan of a patient with an imaging system;
   monitoring the patient, with a patient monitoring device;

analyzing The output of the patient monitoring device to detect abnormalities; and upon detection of an abnormality issuing an alarm on the imaging system; and wherein upon detection of a particular predetermined abnormality, adjusting an output of a transmitter of the imaging system to a non-zero value.

9. A method, according to claim 8, wherein the step of analyzing the output of the patient monitoring device is performed by the imaging system.

10. A method, according to claim 8, further comprising:

upon detection of a predetermined abnormality issuing an alert to a remote device.

11. A method, according to claim 8, wherein the step of monitoring the patient comprises obtaining an ECG trace.

12. A method, according to claim 8, wherein the step of analyzing the output of the patient monitoring device to detect abnormalities comprises analyzing an ECG trace to detect arrhythmia.

13. A computer readable medium, encoded with routines for causing a processor in an imaging system to perform the following actions;

control a scanning device of the imaging system;

receive a data stream from a patient monitoring device;

analyze the data stream to detect abnormalities; and upon detection of an abnormality, issuing an alarm on the imaging system; and wherein upon detection of a particular predetermined abnormality, adjusting an output of the scanning device to 4 non-zero value.

14. A computer readable medium, according to claim 13, further comprising:

upon detection of a predetermined abnormality issuing an alert to a remote device.

15. An ultrasound system comprising:

an imaging front end;

means for receiving and analyzing a signal from a patient monitoring device to detect abnormalities; and control means for issuing an alarm to a user of the ultrasound system upon detection of a predetermined abnormality;

wherein the control means further adjusts the output operation of the imaging front end to a non-zero value upon detection of a particular predetermined abnormality.

16. An ultrasound system, as set forth in claim 15, further comprising communication means for communicating with a remote device and wherein the control means further transmits a message, using the communication means, to the remote device upon detection of a predetermined abnormality.

17. A medical system comprising:

a patient monitoring device that monitors physiological parameters of a patient and outputs a signal indicating values for the parameters; and an imaging system including:

an imaging probe that directs energy into a patient;

a signal analyzer, in communication with the patient monitoring device, that analyzes the signal from the patient monitoring device and outputs an abnormality signal indicating irregularities in parameters monitored; and a controller monitoring the signal from the signal analyzer and, when a predetermined abnormality signal is output, reduces the energy output by the imaging probe to a non-zero value.

18. A patient monitoring system that interfaces with an ultrasound system that isonifies a patient with an ultrasound signal having a defined power level, the patient monitoring system comprising:

a monitoring device that monitors physiological parameters of a patient and outputs a signal indicating values for the parameters; and a signal analyzer, in communication with the monitoring device, that analyzes the signal from the patient monitoring device and, upon detection of a predetermined condition, outputs a signal to the ultrasound system directing the ultrasound system to adjust the power level of the ultrasound signal to a non-zero value.

19. A medical system comprising:

a patient monitoring device that monitors physiological parameters of a patient and outputs a signal indicating values for the parameters;

an automated drug delivery system that delivers a drug to the patient; and an imaging system including:

an imaging probe that directs energy into a patient;

a signal analyzer, in communication with the patient monitoring device, that analyzes the signal from the patient monitoring device and outputs an abnormality signal indicating irregularities in parameters monitored; and a controller monitoring the signal from the signal analyzer and, when a predetermined abnormality signal is output, transmits a signal to the automated drug delivery system to modify the delivery of the drug to the patient;

wherein the controller, upon output of a predetermined signal by the signal analyzer changes the energy output by the imaging probe to a non-zero value.

\* \* \* \* \*